United States Patent
Brown, Jr. et al.

(10) Patent No.: US 7,172,858 B2
(45) Date of Patent: Feb. 6, 2007

(54) BLOOD-BASED ASSAY FOR DYSFERLINOPATHIES

(75) Inventors: Robert H. Brown, Jr., Needham, MA (US); Meng F. Ho, Singapore (SG); Isabel Illa, Barcelona (ES); Eduardo Gallardo, Badalona (ES)

(73) Assignees: The General Hospital Corporation, Boston, MA (US); Hospital Sta Creu I Sant Pau, Barcelona (ES)

( * ) Notice: Subject to any disclaimer, the term of this patent is extended or adjusted under 35 U.S.C. 154(b) by 266 days.

(21) Appl. No.: 10/306,662

(22) Filed: Nov. 27, 2002

(65) Prior Publication Data

US 2003/0165937 A1 Sep. 4, 2003

Related U.S. Application Data

(60) Provisional application No. 60/333,895, filed on Nov. 28, 2001.

(51) Int. Cl.
*C12Q 1/25* (2006.01)
*C12Q 1/68* (2006.01)
*G01N 33/53* (2006.01)
*G01N 33/48* (2006.01)
*G01N 33/49* (2006.01)

(52) U.S. Cl. ............................... 435/4; 435/6; 435/7.1; 436/501

(58) Field of Classification Search .................... 435/4, 435/6, 7.1; 436/501
See application file for complete search history.

(56) References Cited

U.S. PATENT DOCUMENTS 6,300,092 B1  10/2001  Khodadoust et al. ......... 435/16

FOREIGN PATENT DOCUMENTS

| EP | 1130094 A2 | 9/2001 |
|---|---|---|
| WO | WO 9954460 A2 | 10/1999 |
| WO | WO 9964626 A2 | 12/1999 |
| WO | WO 00/11157 * | 3/2000 |
| WO | WO 200011016 | 3/2000 |
| WO | WO 200011157 | 3/2000 |
| WO | WO 200044910 A1 | 8/2000 |
| WO | WO 200055180 A2 | 9/2000 |
| WO | WO 200136475 A2 | 5/2001 |
| WO | WO 200151504 A1 | 7/2001 |
| WO | WO 200157273 A2 | 8/2001 |
| WO | WO 200170972 A2 | 9/2001 |

OTHER PUBLICATIONS

Vainzof et al., Dysferlin Protein Analysis in Limb-Girdle Muscular Dystrophies (2001), J. Mol. Neurosci. 17: 71-80.*
Roberts et al., Direct diagnosis of carriers of Duchenne and Becker muscular dystrophy by amplification of lymphocyte RNA (1990), The Lancet 336 (8730): 1523-1526.*
Piccolo et al., Intracellular Accumulation and Reduced Sarcolemmal Expression of Dysferlin in Limb-Girdle Muscular Dystrophies (2000), Ann. Neur. 48(26): 902-912.*
Emery, The muscular dystrophies (2002), The Lancet 359: 687-695.*
Achanzar et al. "A nematode gene required for sperm vesicle fusion" *J. Cell. Sci.* 110:1073-1081 (1997).
Anderson et al. "Dysferlin is a plasma membrane protein and is expressed early in human development" *Hum. Mol. Genet.* 8(6):1141 (1999).
Anderson et al. "Dysferlin is a plasma membrane protein and is expressed early in human development" *Hum. Mol. Genet.* 8(5):855-861 (1999).
Anderson et al. "Multiplex Western blotting system for the analysis of muscular dystrophy proteins" *Am. J. Pathol.* 154(4):1017-1022 (1999).
Argov et al. "Muscular dystrophy due to dysferlin deficiency in Libyan Jews: clinical and genetic features" *Brain* 123(6):1229-1237 (2000).
Bushby "The limb-girdle muscular dystrophies—multiple genes, multiple mechanisms" *Human Molecular Genetics* 8(10):1875-1882 (1999).
Fanin et al. "Calpain-3 and dysferlin protein screening in patients with limb-girdle dystrophy and myopathy" *Neurology* 56(5):660-665 (2001).
McNally et al. "Splicing mutation in dysferlin produces limb-girdle muscular dystrophy with inflammation" *Am. J. Med. Genet.* 91(4):305-312 (2000).
Piccolo et al. "Intracellular accumulation and reduced sarcolemmal expression of dysferlin in limb-girdle muscular dystrophies" *Ann Neurol.* 48(6):902-912 (2000).
Nakagawa et al. "Phenotypic variation in a large Japanese family with Miyoshi myopathy with nonsense mutation in exon 19 of dysferlin gene" *J. Neurol. Sic.* 184(1):15-19 (2001).

* cited by examiner

*Primary Examiner*—Janet L. Andres
*Assistant Examiner*—Steven H. Standley
(74) *Attorney, Agent, or Firm*—Hamilton, Brook, Smith & Reynolds, P.C.

(57) ABSTRACT

It has been discovered that dysferlin is expressed in blood and that individuals who lack dysferlin in muscle also lack it in CD14(+) cells. Based on these discoveries, blood-based tests for dysferlin expression and uses of such tests are described.

16 Claims, 3 Drawing Sheets

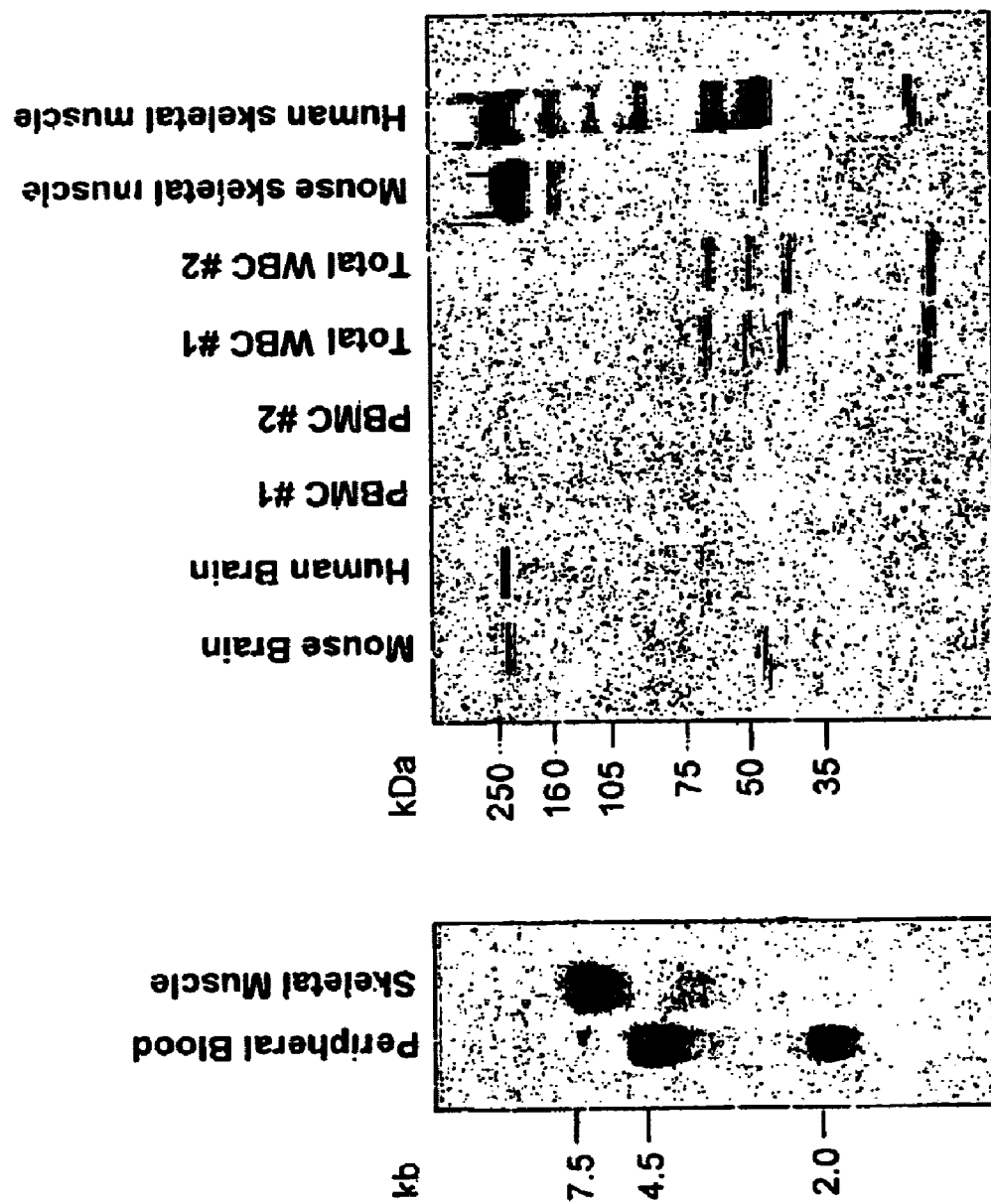

BLOOD-BASED ASSAY FOR DYSFERLINOPATHIES

The present application claims the benefit of the filing date of U.S. Ser. No. 60/333,895, which was filed on Nov. 28, 2001. The contents of U.S. Ser. No. 60/333,895 are hereby incorporated by reference in the present application in their entirety.

TECHNICAL FIELD

This invention relates to muscular dystrophy, and more particularly to diagnostic tests for muscular dystrophy.

BACKGROUND

Limb girdle muscular dystrophy 2B (LGMD) and Miyoshi myopathy (MM) are both characterized by autosomal recessive inheritance, adult onset, and marked elevations of the muscle enzyme creatine kinase (Bushby, 1999, Brain 122:1403–1420). Both have been shown to arise from defects in a gene that encodes dysferlin (Bashir et al., 1998, Nat. Genet. 20:37–42; Liu et al., 1998, Nat. Genet. 20:31–36). The same mutation in the dysferlin gene can cause different clinical presentations, even among members of the same family (Illarioshkin et al., 2000, Neurology 55:1931–1933; Weiler et al., 1999, Hum. Mol. Genet. 8:871–877; Weiler et al., 1996, Am. J. Hum. Genet. 59:872–878). In addition, an anterior distal myopathy has been linked to a dysferlin mutation (Illa et al., 2001, Ann. Neurol. 49:130–134). Thus, there is considerable clinical heterogeneity among dysferlinopathies.

The dysferlin gene is large, comprising 55 exons that span a genomic region of over 150 kb (Aoki et al., 2001, Neurology 57:271–278). It encodes a membrane-associated 237 kDa dysferlin protein composed of 2,080 amino acids that is membrane-associated (Anderson et al., 1999, Hum. Mol. Genet. 8:855–861; Matsuda et al., 1999, Neurology 53:1119–1122; Selcen et al., 2001, Neurology 56:1472–81).

At present, an accurate diagnosis of dysferlinopathy requires a combination of clinical evaluation, protein studies (immunoblot or immunohistochemical analysis) of muscle tissue, and/or direct gene analysis. Moreover, defects in the dysferlin gene are predominantly single nucleotide changes with no evidence of recurrent mutations, gross rearrangements, or mutational hotspots to aid detection (Liu et al., 1998, Nat. Genet. 20:31–36; Aoki et al., 2001, Neurology 57:271–278; Anderson et al., 1999, Hum. Mol. Genet. 8:855–861). For these reasons, DNA-based diagnosis is difficult to use as an initial screening strategy to distinguish dysferlinopathies from the other forms of muscular dystrophy.

SUMMARY

The invention is based, in part, on the discoveries that dysferlin is expressed in a subpopulation of peripheral white blood cells (monocytes or CD 14(+) cells), and that individuals who lack dysferlin in muscle also lack it in CD14(+) cells. These discoveries led to the invention of a blood-based test for aberrant expression of dysferlin. Such a test can be used, e.g., as a test for dysferlinopathy and provides a method of monitoring therapy administered to treat a dysferlinopathy.

In one embodiment, the invention provides a method of determining whether dysferlin is expressed in a mammal. The method includes the steps of providing a blood sample from the mammal and assaying the blood sample for the presence of dysferlin expression. Dysferlin expression can be assayed by detecting dysferlin nucleic acid expression or detecting dysferlin protein expression (e.g., using an immunologic assay). The method can include the step of determining the level of dysferlin mRNA or dysferlin protein in the blood sample. In some embodiments the method includes the step of comparing the level of dysferlin protein or dysferlin mRNA in the blood sample to a reference. For example, in some aspects of the invention, a lower level of dysferlin expression in the blood sample compared to the reference indicates the presence of a dysferlinopathy in the mammal. In certain embodiments, the mammal is suspected of having a dysferlinopathy (e.g., limb girdle muscular dystrophy 2B (LGMD) or Miyoshi myopathy (MM)). The mammal may be, e.g., a mouse or a human.

The invention includes a method of determining whether a mammal has a dysferlinopathy, is predisposed to having a dysferlinopathy, or is a genetic carrier for a dysferlinopathy. The method includes the steps of providing a blood sample from the mammal; and determining the level of dysferlin expression in the blood sample, such that a level lower than a predetermined value is an indication that the mammal is has a dysferlinopathy, is predisposed to having a dysferlinopathy or is a genetic carrier for a dysferlinopathy.

In another embodiment, the invention provides a method for determining whether a therapy for a dysferlinopathy is effective in a mammal. The method includes the steps of providing a blood sample from the mammal following treatment with the therapy and determining the level of dysferlin expression in the blood sample such that a level of dysferlin expression that is higher than the level of dysferlin expression in a blood sample obtained from the mammal prior to the initiation of therapy is an indication that the therapy is effective.

In certain aspects of the invention, the step of determining the level of dysferlin expression includes exposing the blood sample to a nucleic acid molecule that hybridizes to a dysferlin mRNA under stringent conditions.

In other embodiments of the invention, the step of determining the level of dysferlin expression includes detecting the presence of dysferlin polypeptide, e.g., by contacting the blood sample to an antibody that selectively binds to dysferlin.

In some embodiments of the invention, the mammal is a mouse or human. In other aspects of the invention, the dysferlinopathy is LGMD or MM.

A dysferlinopathy, as used herein, refers to a disorder that is associated with an aberrant pattern of dysferlin expression. Such disorders are known in the art and include limb girdle muscular dystrophy 2B and Miyoshi myopathy. "Misexpression or aberrant expression," as used herein, refers to a pattern of gene expression that differs from that in a normal individual (i.e., an individual that does not have a dysferlinopathy, is not predisposed to a dysferlinopathy, and is not a carrier of a gene sequence that is associated with a dysferlinopathy; also referred to wild-type or normal control), at the RNA or protein level in a blood cell (e.g., a monocyte). It includes: expression at non-normal levels, i.e., over- or under-expression of dysferlin; a pattern of expression that differs from normal in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing size, amino acid sequence, post-translational modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus. It also includes aberrant or misexpression that occurs because of an altered rate of turnover compared to normal of a dysferlin polypeptide or RNA (for example, an increased rate of dysferlin polypeptide degradation). In general, misexpression or aberrant expression is a decrease in expression of a dysferlin RNA or polypeptide. In general, "mRNA" refers to poly A+.

An animal, e.g., human, is "at risk for" or "predisposed to" developing a condition if there is an increased probability that it will develop the condition compared to a population (e.g., the general population, an age-matched population, a population of the same sex). The increased probability can be due to one or a combination of factors including the presence of specific alleles/mutations of a gene or exposure to a particular environment. For example, an individual is at risk for developing a dysferlinopathy when he or she exhibits decreased levels of dysferlin expression (e.g., in a blood cell such as a monocyte) compared to a normal control population.

The amount of expression of a dysferlin in a test blood cell or blood sample (e.g., a cell from an individual suspected of having a dysferlinopathy, being predisposed to a dysferlinopathy, or being a genetic carrier for a dysferlin gene sequence associated with a dysferlinopathy) may be evaluated by comparing it to a predetermined value or reference (e.g., the level of expression in a normal blood cell), or to expression in a normal control cell.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A depicts the results of a Northern blot showing dysferlin gene expression in peripheral blood mononuclear cells from a healthy individual, with a probe corresponding to nucleotides 5364–5732 of the dysferlin cDNA.

FIG. 1B depicts the results of a Western blot showing dysferlin protein expression in multiple tissues using the NCL-Hamlet monoclonal antibody. The positive controls include skeletal muscle and brain tissues from mouse and human.

DETAILED DESCRIPTION

Figure 1E:
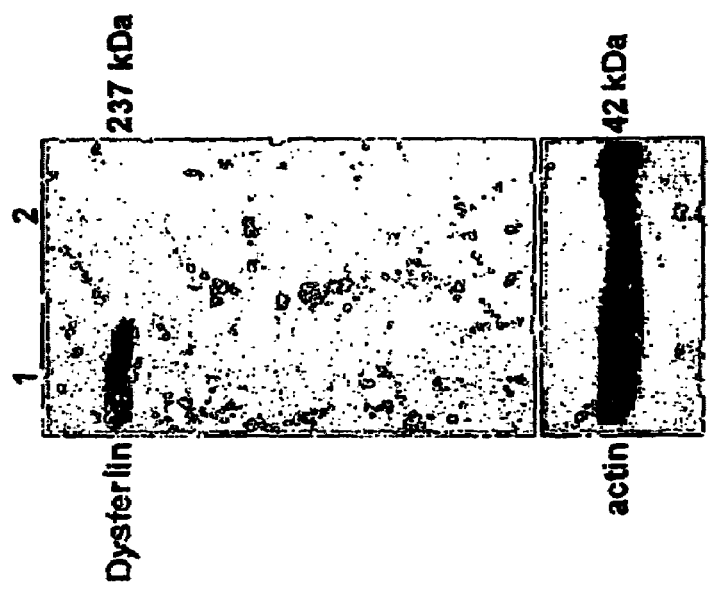
FIG. 1E depicts the results of a Western blot analysis of dysferlin expression in CD14-positive cells (lane 1) and CD14-negative cells (lane 2). Immunoblotting of the 42kDA actin antigen served as a positive control in both preparations (lanes 1 and 2, bottom panel).
Figure 1D:
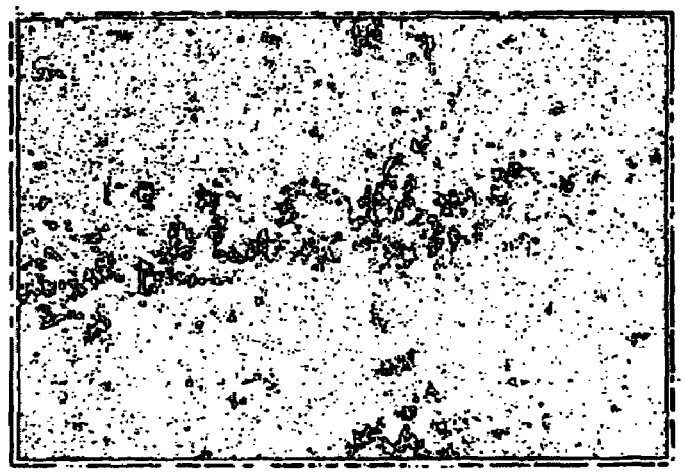
FIGS. 1C–1D depict the results of immunocytochemical analysis of dysferlin expression in CD14-negative cells (FIG. 1C) and CD14-positive cells (FIG. 1D).

Screening for defective protein expression by immunoblot analysis has proved to be a reliable and rapid means for differential diagnosis in muscular dystrophies (Anderson and Davison, 1999, Am. J. Pathol. 154:1017–1022). However, current methods require muscle biopsy samples. The present invention provides methods useful for diagnosing dysferlinopathies. In particular the methods use non-muscle tissue and a less invasive sampling technique. Although dysferlin has been found to be expressed in certain non-muscle tissues including heart, placenta, and kidney (Liu et al., 1998, supra; Matsuda et al., 1999, supra), it was not previously known to be expressed in peripheral blood cells. It has been discovered that dysferlin is expressed in monocytes and that dysferlin expression in monocytes correlates with its expression in skeletal muscle (Table 1). Thus, the detection of dysferlin expression in monocytes can be used as a blood-based diagnostic assay for dysferlinopathies, e.g., LGMD 2B and MM.

The new blood-based diagnostic assay offers several advantages over current methods of muscle immunodiagnosis. The methods of the invention overcome certain problems associated with the handling and storage of muscle specimens. The method is accomplished using a less invasive tissue sampling method compared to muscle biopsy. The less invasive method should make it easier and less debilitating to obtain samples from patients to confirm diagnosis, to guide further testing or to asses the efficacy of a treatment. Moreover, collection of samples for use in the methods will not require the operating theater, which is a significant cost-savings benefit.

In addition to diagnostic applications, dysferlin expression in monocytes provides a new paradigm that can be used to study the biological function of this protein in a non-muscle cell type that is readily accessible and amenable to in vitro functional assays. Also, the invention may provide a convenient method for monitoring the progression of a dysferlinopathy in an individual, and for monitoring the effect of a therapy intended to increase the levels of dysferlin in an individual, e.g., to monitor the efficacy of a treatment by monitoring dysferlin levels in blood rather than skeletal muscle.

The methods of the invention are also useful for identifying disorders in which dysferlin expression is altered as a secondary effect (e.g., in a muscular dystrophy caused by something other than a mutation in a dysferlin gene). Identification of patients with reduced dysferlin expression but without defects in the dysferlin gene could, for example, lead to the discovery of proteins that normally associate with or control expression of dysferlin and help elucidate the pathophysiological pathway involved in dysferlinopathies.

The invention employs methods of detecting dysferlin expression in a blood sample. The method can employ detection of a dysferlin nucleic acid or a dysferlin polypeptide. Methods of preparing blood cells, e.g., monocytes, for detecting nucleic acids and polypeptides are known in the art.

Dysferlin Nucleic Acids

In some embodiments of the invention, a test blood sample is assayed for dysferlin expression by detecting RNA. Thus, various methods of the invention employ an isolated or purified nucleic acid molecule (or complement thereof) that encodes a dysferlin, e.g., a full-length dysferlin protein or a fragment thereof, e.g., an antigenic fragment of a dysferlin protein, as well as nucleic acid molecules that hybridize, e.g., under highly stringent conditions, to a nucleic acid molecule that encodes dysferlin and nucleic acid molecules having a defined degree of sequence identity (e.g., at least about 60%, 65%, 70%, 75%, 80%, 85%, 90%, 91%, 92%, 93%, 94%, 95%, 96%, 97%, 98%, or 99% identity), to a nucleic acid molecule encoding a dysferlin (e.g., Genbank Accession nos. XM 034329 (human mRNA), XM 010780 (human mRNA), NM 003494 (human mRNA), AF075575 (human mRNA), AJ007973 (human genomic DNA), and AF188290 (mus musculus mRNA)). Dysferlin cDNA sequences are disclosed in WO 00/11157 and WO 00/11016 and are herein incorporated by reference.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, e.g., at least 40%, at least 50%, at least 60%, or at least 70%, 80%, 90%, or 100% of the length of the reference sequence (e.g., when aligning a second sequence to a dysferlin amino acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444–453, 1970) algorithm which has been incorporated into the GAP program in the GCG software package (available on the internet at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available on the internet at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller (CABIOS (1989) 4:11–17) which has been incorporated into the ALIGN program (version 2.0), using a PAM120 weight residue table, a gap length penalty of 12 and a gap penalty of 4.

As used herein, the term "hybridizes under stringent conditions" describes conditions for hybridization and washing. Stringent conditions are known to those skilled in the art and can be found in Current Protocols in Molecular Biology (John Wiley & Sons, N.Y. (1989), 6.3.1–6.3.6). Aqueous and non-aqueous methods are described in that reference and either can be used. An example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Generally, stringent hybridization conditions are hybridization in 6× sodium chloride/sodium citrate (SSC) at about 45° C., followed by one or more washes in 0.2×SSC, 0.1% SDS at 65° C. Other stringency conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C.

Dysferlin probes and primers are useful in many detection methods. Typically a probe/primer is an isolated or purified oligonucleotide. The oligonucleotide typically includes a region of nucleotide sequence that hybridizes under stringent conditions to at least about 7, 12, or 15, preferably about 20 or 25, more preferably about 30, 35, 40, 45, 50, 55, 60, 65, or 75 consecutive nucleotides of a dysferlin sense or antisense sequence or of a naturally occurring allelic variant or mutant of a dysferlin nucleic acid sequence.

Primers suitable for use in a PCR, which can be used to amplify a selected region of a dysferlin sequence, are useful in certain methods of the invention. The primers should be at least 5, 10, or 50 base pairs in length and are generally fewer than 100, or less than 200, base pairs in length.

Other useful nucleic acid molecules are more than 260, 300, 400, 500, 600, 700, 800, 900, 1000, or 1100 or more nucleotides in length and hybridize under stringent hybridization conditions to a dysferlin nucleic acid molecule.

Also useful in the methods of the invention are nucleic acid molecules that are naturally occurring, such as allelic variants (same locus), homologs (different locus), and orthologs (different organism), or can be non-naturally occurring. Other useful variants include sequences that include mutations associated with dysferlinopathy. Examples of such mutations can be found in, e.g., in WO 11157 and WO 11016. Variation can occur in either or both the coding and non-coding regions. Such variations in the coding region can produce both conservative and non-conservative amino acid substitutions.

Useful allelic variants of dysferlin (e.g., that are useful as antigens or reference proteins) include both functional and non-functional proteins. Functional allelic variants are naturally occurring amino acid sequence variants of the dysferlin protein within a population that maintain the ability to mediate dysferlin biological activity (e.g., an animal homozygous for the sequence encoding the allelic variant has normal muscle function). Functional allelic variants will typically contain only conservative substitution of one or more amino acids of a dysferlin sequence, or substitution, deletion or insertion of non-critical residues of the protein. Non-functional allelic variants are naturally-occurring amino acid sequence variants of the dysferlin protein that do not have the ability to mediate dysferlin biological activity in an animal carrying two copies of the gene encoding the dysferlin variant (i.e., the animal develops a dysferlinopathy). Non-functional allelic variants will typically contain a non-conservative substitution, a deletion, insertion, or a premature truncation of the amino acid sequence of a dysferlin protein or a substitution, insertion, or deletion in critical residues or critical regions of the protein.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Isolated Dysferlin Polypeptides

Isolated dysferlin protein, or a fragment thereof, e.g., a biologically active portion, can be used, e.g., as an immunogen or antigen to raise or test (or more generally to bind) anti-dysferlin antibodies useful in diagnostic assays and in the preparation of therapeutic compositions. Dysferlin protein can be isolated from cells or tissue sources using standard protein purification techniques. Dysferlin protein or fragments thereof can be produced by recombinant DNA techniques or synthesized chemically. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

Useful dysferlin protein or fragments thereof can differ from a known dysferlin protein sequence (e.g., it differs by at least one, but by fewer than 15, 10, or 5 amino acid residues or by at least one residue but fewer than 20%, 15%, 10% or 5% of the residues in it). Useful proteins include an amino acid sequence at least about 60%, 65%, 70%, 75%, 80%, 85%, 90%, 95%, 98%, or more identical to a known dysferlin protein sequence.

Anti-Dysferlin Antibodies

Antibodies raised against a dysferlin polypeptide are useful in certain embodiments of the invention. Such antibodies are available commercially or can be generated using methods known in the art.

Anti-dysferlin antibodies can be used diagnostically and may be useful in therapeutic applications. The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments that can be generated by treating the antibody with an enzyme such as pepsin.

The antibody can be a polyclonal, monoclonal, recombinant, e.g., a chimeric or humanized, fully-human, non-human (e.g., murine), or single chain antibody. In one embodiment, it has effector function and can fix complement. The antibody can be coupled to an imaging agent.

A full-length dysferlin protein or, antigenic peptide fragment of dysferlin can be used to (a) generate antibodies that are useful in certain embodiments of the invention, or (b) can be used to identify anti-dysferlin antibodies made with other immunogens, e.g., monocytes, monocytes membrane preparations, and the like.

Preferred epitopes encompassed by the antigenic peptide are generally regions of dysferlin that are located on the surface of the protein, e.g., hydrophilic regions, as well as regions with high antigenicity. For example, an Emini surface probability analysis of a dysferlin protein sequence can be used to indicate the regions that have a particularly high probability of being localized to the surface of the dysferlin protein and are thus likely to constitute surface residues useful for targeting antibody production.

The anti-dysferlin antibody can be a single chain antibody. A single-chain antibody (scFV) may be engineered (see, for example, Colcher, et al., 1999, Ann. N.Y. Acad. Sci. 880:263–80; and Reiter, 1996, Clin. Cancer Res. 2:245–52). The single chain antibody can be dimerized or multimerized to generate multivalent antibodies having specificities for different epitopes of the same target dysferlin protein.

In some embodiments, the antibody has reduced or no ability to bind an Fc receptor, e.g., it is an isotype, subtype, fragment or other mutant, which does not support binding to an Fc receptor, e.g., it has a mutagenized or deleted Fc receptor binding region.

An anti-dysferlin antibody (e.g., monoclonal antibody) for use in methods of the invention can be used to isolate dysferlin from a blood sample by standard techniques, such as affinity chromatography or immunoprecipitation. An anti-dysferlin antibody can be used to detect dysferlin protein (e.g., in a cellular lysate or cell supernatant) to evaluate the abundance (i.e., amount) and pattern of expression of the protein. For example, in individuals having a dysferlinopathy, the amount of dysferlin detectable in a blood sample using an antibody is significantly less than the amount detected in a blood sample from an individual that does not have a dysferlinopathy. In some cases, no dysferlin immunoreactivity is detected in the blood sample from an individual having a dysferlinopathy. Anti-dysferlin antibodies can be used diagnostically to monitor dysferlin protein amounts in blood (e.g., monocytes) as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, green fluorescent protein (GFP), or phycoerythrin; an example of a luminescent material isluminol; examples of bioluminescent materials include luciferase, luciferin, and aequorin, and examples of suitable radioactive materials include $^{125}I$, $^{131}I$, $^{35}S$, or $^{3}H$.

Predictive Medicine

Certain embodiments of the present invention pertain to the field of predictive medicine in which diagnostic assays, prognostic assays, and monitoring of clinical trials are used for prognostic (predictive) purposes to thereby treat an individual. For example, one could determine if a subject is at risk for a disorder (i.e., is predisposed to) a dysferlinopathy. In general, such disorders are related to a lesion in, or the misexpression of, a gene that encodes a dysferlin polypeptide. However, the methods of the invention are also useful for monitoring dysferlin in disorders in which the amount of dysferlin expression in blood is a secondary effect (e.g., due to a defect in a gene other than a dysferlin gene).

Diagnostic and Prognostic Assays

The presence, level, or absence of dysferlin protein or nucleic acid in a blood sample (e.g., monocyte) can be evaluated by obtaining a blood sample from a test subject (e.g., an individual suspected of having a dysferlinopathy such as LGMD or MM) and contacting the blood sample with a compound or an agent capable of detecting dysferlin protein or nucleic acid (e.g., mRNA) that encodes dysferlin protein or a fragment thereof (e.g., a degradation product of dysferlin) such that the presence of dysferlin protein or nucleic acid is detected in the blood sample. The level of expression of the dysferlin gene can be measured in a number of ways, including, but not limited to: measuring dysferlin mRNA in a blood sample or measuring the amount of protein encoded by the dysferlin genes in a blood sample. Such methods can measure, e.g., the absolute level or relative level of a nucleic acid or protein. The level of dysferlin mRNA in a cell can be determined both by in situ and by in vitro formats.

The term "blood sample" includes whole blood, serum, plasma, a sample enriched for specific cell types (e.g., monocytes), and a sample containing blood cells that has been processed to enhance detection of nucleic acids or proteins. In general, the blood sample will be from an individual having or suspected of having a dysferlinopathy. The sample can also be from an individual suspected of being predisposed to having a dysferlinopathy or of having a dysferlin gene associated with a dysferlinopathy (i.e., the individual is a carrier for a dysferlinopathy).

Dysferlin mRNA can be used in hybridization or amplification assays that include, but are not limited to, Southern or Northern analyses, polymerase chain reaction analyses, and probe arrays. The mRNA can be isolated using methods known in the art. In general, poly A+ from a cell (e.g., blood cell) is used for such assays. The RNA can be isolated from a whole blood sample or a sample that is enriched for specific cell types (e.g., monocytes). One diagnostic method for the detection of mRNA levels involves contacting the isolated mRNA with a nucleic acid molecule (probe) that can hybridize to the mRNA of interest. The nucleic acid probe can be, for example, a full-length, single-stranded antisense dysferlin nucleic acid, such as a nucleic acid of any one of Genbank accession nos. XM 034329 (human mRNA), XM 010780 (human mRNA), NM 003494 (human mRNA), AF075575 (human mRNA), AJ007973 (human genomic DNA), and AF188290 (mus musculus mRNA), or a portion thereof, such as an oligonucleotide of at least 15, 30, 50, 100, 250, or 500 nucleotides in length and sufficient to specifically hybridize under stringent conditions to a dysferlin mRNA. Other suitable probes for use in the invention include, e.g., those described herein.

In one format, mRNA (or cDNA) is immobilized on a surface and contacted with the probes, for example, by running isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of dysferlin mRNA in a blood sample.

The level of dysferlin mRNA in a sample can be evaluated with nucleic acid amplification, e.g., by RT-PCR (Mullis, U.S. Pat. No. 4,683,202), ligase chain reaction (Barany, 1991, Proc. Natl. Acad. Sci. USA 88:189–193), self-sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. Under appropriate conditions and with appropriate reagents, such primers permit the amplification of a nucleic acid molecule comprising the nucleotide sequence between the primers. Examples of such primers are described in WO 00/11157 and WO 11016.

For in situ methods, a blood sample can be prepared/processed and immobilized on a support, typically a glass slide, and then contacted with a probe that can hybridize to dysferlin mRNA.

In another embodiment, the methods include further contacting a control sample with a compound or agent capable of detecting dysferlin mRNA or cDNA, and comparing the presence of dysferlin mRNA or cDNA in the control sample with the presence of dysferlin mRNA or cDNA in the test sample.

A variety of methods can be used to detect a dysferlin polypeptide or to determine the amount of dysferlin protein present in a sample. In some aspects of the invention, the amount of a dysferlin polypeptide in a test blood sample relative to a reference is determined. The reference can be a predetermined standard amount or a sample (e.g., control) that is evaluated concurrently with the test sample. In general, these methods include contacting an agent that selectively binds to the protein, such as an antibody, with a blood sample, to evaluate the level of protein in the sample. In some embodiments of the invention, the antibody bears a detectable label. Antibodies can be polyclonal, or more preferably, monoclonal. An intact antibody or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect dysferlin protein in a blood sample in vitro. In vitro techniques for detection of dysferlin protein present in a blood sample include enzyme linked immunosorbent assays (ELISAs), immunoprecipitations, immunofluorescence, enzyme immunoassay (EIA), radioimmunoassay (RIA), and Western blot analysis.

The methods can further include contacting a control sample with a compound or agent capable of detecting dysferlin protein, and comparing the level of dysferlin protein in the control sample with the presence of dysferlin protein in the test sample.

The invention also includes kits for detecting the presence of dysferlin protein of mRNA in a biological sample. For example, the kit can include a compound or agent capable of detecting dysferlin protein or mRNA in a biological sample, and optionally, a standard. The compound or agent can be packaged in a suitable container. The kit can further comprise instructions for using the kit to detect dysferlin protein or nucleic acid in blood cells.

For antibody-based kits, the kit can include: (1) a first antibody (e.g., attached to a solid support) that binds to a dysferlin polypeptide; and optionally (2) a second, different antibody that binds to either the dysferlin or the first antibody and is conjugated to a detectable agent. Optionally, the kit also contains a vial suitable for containing a blood sample and instructions for use in the method of the invention.

For oligonucleotide-based kits, the kit can include: (1) an oligonucleotide, e.g., a detectably-labeled oligonucleotide, that hybridizes to a dysferlin mRNA or (2) a pair of primers useful for amplifying a nucleic acid molecule corresponding to a dysferlin mRNA. The kit can also include at least one of a buffering agent, a preservative, or a protein-stablizing agent. The kit can also include components necessary for detecting the detectable agent (e.g., an enzyme or a substrate). The kit can also contain a control sample (e.g., a positive or negative control sample) or a series of control samples that can be assayed and compared to the test sample. Each component of the kit can be enclosed within a separate container and all of the various containers can be within a single package, along with instructions for interpreting the results of the assays performed using the kit.

The diagnostic methods described herein can identify subjects having, or at risk of developing, a disease or disorder associated with misexpressed, aberrant or unwanted dysferlin expression. The prognostic assays described herein can be used to determine whether a subject is likely to develop symptoms of a dysferlinopathy or whether a subject can be administered an agent (e.g., an agonist, antagonist, peptidomimetic, protein, peptide, nucleic acid, small molecule, or other drug candidate) to treat a dysferlinopathy. For example, such methods can be used to determine whether a subject can be effectively treated with an agent that increases dysferlin expression or activity.

The methods of the invention can also be used to detect genetic alterations in a dysferlin gene, thereby determining if a subject with the altered gene is at risk for developing a dysferlinopathy. The methods include detecting, in a sample from the subject, the presence or absence of a genetic alteration characterized by at least one of an alteration affecting the integrity of a mRNA encoding a dysferlin protein, or causing the misexpression of the dysferlin gene. For example, such genetic alterations can be detected by ascertaining the existence of at least one of 1) an alteration in the level of an mRNA transcript of a dysferlin gene, 2) the presence of a non-wild-type splicing pattern of an mRNA transcript of a dysferlin gene, 3) a non-wild-type level of a dysferlin protein, 4) inappropriate post-translational modification of a dysferlin protein, and 5) an alteration in the sequence of a dysferlin transcript. Such methods are known in the art.

An alteration in the sequence of a dysferlin mRNA can be detected without a probe/primer in a polymerase chain reaction, such as anchor PCR or RACE-PCR, or alternatively in a ligation chain reaction (LCR), which can be particularly useful for detecting point mutations in the dysferlin gene. This method can include the steps of collecting a sample of blood cells from a subject, isolating poly A+ (mRNA) from the sample, contacting the mRNA with one or more primers that specifically hybridize to a dysferlin nucleic acid sequence under conditions such that hybridization and amplification of the dysferlin sequence occurs (if present), and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations in dysferlin genes such as those described in WO 11157 and WO 11016.

Alternative amplification methods include: self sustained sequence replication (Guatelli et al., 1990, Proc. Natl. Acad. Sci. USA 87:1874–1878), a transcriptional amplification system (Kwoh et al., 1989, Proc. Natl. Acad. Sci. USA 86:1173–1177), Q-Beta Replicase (Lizardi et al., 1988, Bio-Technology 6:1197), and other nucleic acid amplification methods, followed by the detection of the amplified molecules using techniques known to those of skill in the art.

In another embodiment, mutations in a dysferlin mRNA in a blood cell can be identified by detecting alterations in ribozyme cleavage patterns. In such methods, sequence specific ribozymes (see, for example, U.S. Pat. No. 5,498, 531) can be used to score for the presence of specific mutations by development or loss of a ribozyme cleavage site. Alternatively, deoxyribozymes can be used.

In other embodiments, genetic mutations in dysferlin can be identified by hybridizing an mRNA sample obtained from a blood cell (or a cDNA) to probe nucleic acids, e.g., DNA or RNA, by, e.g., two-dimensional arrays, or, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotide probes (Cronin et al., 1996, Human Mutation 7:244–255; Kozal et al., 1996, Nature Medicine 2:753–759). For example, mutations in dysferlin mRNA can be identified in two-dimensional arrays containing light-generated DNA probes as described in Cronin et al., supra. Briefly, a first hybridization array of probes can be used to scan through long stretches of RNA (or cDNA) in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each second hybridization array is composed of parallel probe sets, one complementary to the wild-type gene and the other complementary to the mutant gene.

Other methods for detecting mutations in a dysferlin gene include methods in which protection from cleavage agents is used to detect mismatched bases in RNA/RNA or RNA/DNA heteroduplexes (Myers et al., 1985, Science 230:1242; Cotton et al., 1988, Proc. Natl. Acad. Sci. USA 85:4397; Saleeba et al., 1992, Methods Enzymol. 217:286–295) using mRNA obtained from a blood sample from an individual who is suspected of having a dysferlinopathy.

In still another embodiment, the mismatch cleavage reaction employs one or more enzymes that recognize mismatched base pairs in double-stranded DNA (so called "DNA mismatch repair" enzymes) in defined systems for detecting and mapping point mutations in dysferlin cDNAs obtained from samples of blood cells. For example, the mutY enzyme of *E. coli* cleaves A at G/A mismatches and the thymidine DNA glycosylase from HeLa cells cleaves T at G/T mismatches (Hsu et al., 1994, Carcinogenesis 15:1657–1662; U.S. Pat. No. 5,459,039).

Examples of other techniques for detecting point mutations include but are not limited to selective oligonucleotide hybridization, selective amplification, or selective primer extension (Saiki et al., 1986, Nature 324:163; Saiki et al., 1989, Proc. Natl. Acad. Sci. USA 86:6230) using, e.g., cDNAs generated from blood samples. Alternatively, allele-specific amplification technology that depends on selective PCR amplification may be used in conjunction with the instant invention. Oligonucleotides used as primers for specific amplification of dysferlin sequences expressed in a blood cell may carry the mutation of interest in the center of the molecule (so that amplification depends on differential hybridization) (Gibbs et al., 1989, Nucleic Acids Res. 17:2437–2448) or at the extreme 3' end of one primer where, under appropriate conditions, mismatch can prevent or reduce polymerase extension (Prossner, 1993, Tibtech 11:238). It is anticipated that in certain embodiments, amplification may also be performed using Taq ligase for amplification (Barany, 1991, Proc. Natl. Acad. Sci USA 88:189). In such cases, ligation will occur only if there is a perfect match at the 3' end of the 5' sequence, making it possible to detect the presence of a known mutation at a specific site by looking for the presence or absence of amplification.

Identification of specific dysferlin mutations can also be useful in the application of pharmacogenomics. For example, certain dysferlin mutations, levels of dysferlin expression, or patterns of dysferlin expression may be associated with specific responses to therapeutic interventions for treating a dysferlinopathy. Thus, identification of dysferlin mutations, levels of expression, or patterns of expression may be useful for tailoring a therapeutic regimen to an individual that has a dysferlinopathy.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease involving a dysferlin gene.

EXAMPLES

Example 1

Materials and Methods

Detection of Dysferlin Gene Expression

Total RNA was isolated from whole blood using the QIAamp blood mini kit from Qiagen according to manufacturer's instructions. Approximately 10 µg of total RNA was fractionated on 1% formaldehyde gels and transferred to Hybond™ N+ membranes (Amersham). Hybridization was performed at 65° C. according to standard protocols using a labeled probe corresponding to nucleotides 5364–5732 of the dysferlin cDNA sequence in Genbank accession no. AF 075575. The membranes were washed in 2×SSC, 0.1% SDS for 15 minutes at 65° C. followed by washes in 1×SSC, 0.1% SDS and 0.2×SSC, 0.1% SDS for 15 minutes each.

Such methods can be used to detect dysferlin gene expression in test blood samples.

Isolation of Peripheral Blood Mononuclear Cells and Immunoblot Analysis

Peripheral blood mononuclear cells (PBMC; monocytes) were isolated from whole blood of patients and healthy controls by Ficol™-Paque gradient centrifugation according to manufacturer's instructions (Amersham). PBMC were washed twice in phosphate-buffered saline (PBS) and lysed in ten volumes of protein extraction buffer, M-PER (Pierce, Rockford, Ill.). The sample was centrifuged to pellet cell debris (about 18,000×g for 10 minutes) and the supernatant used for SDS-PAGE analysis of dysferlin. Approximately twenty micrograms of protein were separated on a 4–15% gradient SDS-PAGE gel. Immunoblotting was performed according to standard methods using primary anti-dysferlin monoclonal antibodies (obtained from NCL-Hamlet, Novacastra, UK) at a 1:300 dilution. Immunoreactive bands were detected with the ECL chemiluminescence system (Amersham).

Separation of PBMC into CD14-positive and -negative Cell Populations

For experiments to determine which blood cell type expresses dysferlin, CD14(+) and CD14(−) blood cells were separated. PBMC (approximately $10^7$ cells) were mixed with 20 µl of CD14 antibody-coated microbeads (Milteny Biotec, Germany) and incubated at 6–12° C. for 30 minutes. Unbound cells were removed by washing cells in excess PBS buffer followed by centrifugation at 300×g for ten minutes. The cell pellet was resuspended in PBS to a concentration of $2 \times 10^8$ cells/ml before separation on a MACS (magnetic cell sorter/separation) apparatus according to manufacturer's instructions (Milteny Biotec, Germany).

Immunocytochemistry

Dysferlin protein expression was assayed in blood cells using immunocytochemistry. PBMC were spun onto microscopic slides using a Cytospin™ (Shandon, UK) centrifuge. The cells were then fixed in acetone for ten minutes on ice. For immunocytochemistry, the slides were pre-incubated in PBS (phosphate buffered saline) containing 0.5% BSA and 5% normal goat serum. The sections were then incubated with NCL-Hamlet (Novacastra, UK) diluted 1:20 in PBS containing 5% normal serum for one hour at room temperature. The slides were then washed twice (five minutes each) in PBS Detection of the antibody was carried out using standard techniques. The washed slides were incubated in horseradish peroxidase-labeled secondary antibody (Jackson Immunoresearch, PA) for according to the manufacturer's instructions and visualized by incubating the slides in diaminobenizidine using and ABC staining kit (Vector labs, CA).

Example 2

Detection of Dysferlin Expression in Peripheral Blood Mononuclear Cells (PBMC)

As a first step to develop a non-muscle diagnostic assay for dysferlinopathies, dysferlin gene expression in blood cells of healthy individuals was examined by Northern blot analysis. A weak but distinct band of about 7.5 kb, corresponding to the dysferlin transcript, was detected in total RNA isolated from peripheral blood cells and skeletal muscle (FIG. 1A). Approximately 10 µg of RNA was loaded per lane. Smaller transcripts of around 4.5 kb and 2.0 kb were also detected in the peripheral blood samples, suggesting the presence of tissue-specific splice variants. These data demonstrate that there is dysferlin gene expression in blood cells. Northern blot analysis can thus be used as a method of assaying dysferlin expression, e.g., to determine whether an individual has a dysferlinopathy.

To determine whether dysferlin protein was expressed in blood cells, Western blots of total protein from white blood cell (WBC), peripheral blood mononuclear cells (PBMC), brain and skeletal muscle was screened with an anti-dysferlin monoclonal antibody (NCL-Hamlet) as described in Example 1. A prominent band of approximately 230 kDa corresponding to the dysferlin protein was detected in PBMC, skeletal muscle, and brain but was not detected in total WBC protein in samples. The PBMC and WBC samples were from two unrelated, healthy individuals (FIG. 1B). As PBMC consist primarily of lymphocytes and monocytes, this result suggests that dysferlin is expressed in these cell types. These data demonstrate that dysferlin protein is expressed in at least a subset of blood cells. In immunocytochemistry-based assays for dysferlin, it is generally preferred to use a blood sample that has been enriched for PBMC (monocytes) to increase the sensitivity of the assay.

Example 3

Immunocytochemical Analysis of Dysferlin Expression in PBMC

Figure 1C:

To further define the cell type that expresses dysferlin, PBMC were separated into CD14-positive and -negative cells using magnetic beads coated with CD14 antibodies. This approach distinguishes the two main cell types in PBMC because CD14 is a specific marker for monocytes. As shown in FIGS. 1C and D, immunocytochemical analysis showed dysferlin staining in CD14(+) cells but not in CD14(−) cells. This result was confirmed by Western blot analysis (FIG. 1E). Taken together, these findings indicate that dysferlin expression in blood is primarily in monocytes. The lack of detectable dysferlin protein expression in WBC is likely to be because monocytes constitute only 3 to 7% of total WBC, so that dysferlin constitutes a relatively small amount of the total protein in WBC (FIG. 1A).

Example 4

Diagnostic Applications of Dysferlin Expression in PBMC

To evaluate the accuracy of a blood-based diagnostic assay for dysferlinopathies, a comparison was made of dysferlin expression in PBMC and skeletal muscle in twelve patients that had been diagnosed with LGMD 2B or MM. Dysferlin deficiency in skeletal muscle was confirmed by Western blotting for patient. Immunoblot analyses of PBMC showed dysferlin reactivity in controls (six of six tested) but no dysferlin was detected in any of the twelve blood samples obtained from patients (FIG. 2, Table 1), indicating there is an excellent correlation between dysferlin expression in PBMC and skeletal muscle. These data demonstrate that a blood-based assay can be used to diagnose a dysferlinopathy.

Figure 2:
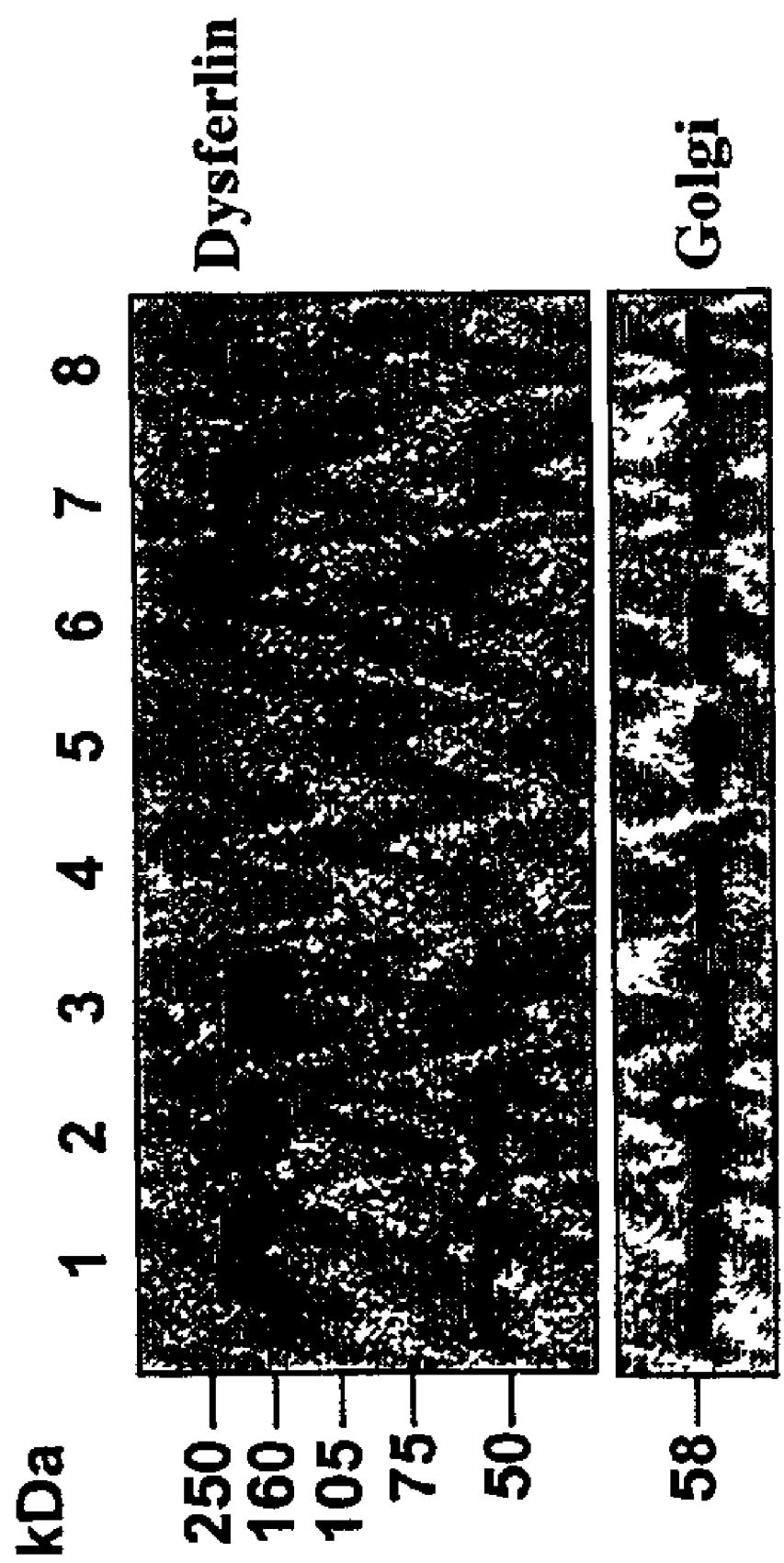
FIG. 2 depicts the results of an immunocytochemical analysis of dysferlin expression in PBMC from healthy controls Miyoshi myopathy patients. Lanes 1, 2, 3, 7, and 8 contain peripheral blood mononuclear cells (PBMC) from normal healthy controls; lanes 4, 5, and 6 (RB 2329, RB 3533, and RB 2079, respectively) are from MM patients (see Table 1 for details of patient genotypes). The effect of delayed processing of blood samples on the stability of the dysferlin protein can be seen by comparing samples that were left for 48 hours (lane 1), 36 hours (lane 2), 24 hours (lanes 3 and 7) and 6 hours (lane 8) before processing for immunoblot analysis.

Since samples cannot always be processed immediately, the effect of delayed processing of blood samples on the stability of the dysferlin protein was also examined using Northern blot analysis as described above. Blood samples that were processed within 36 hours of being drawn showed no evidence of dysferlin degradation while minor degradation can be seen in samples left for 48 hours (FIG. 2). A lower band of about 55 kDa was detected in control samples that were left for 24 hours or more but not in samples that were 6 hours old (FIG. 2). This suggests that the 55 kDa protein is a partially degraded dysferlin product since it is only present in control but not in patient samples. In general, the full-length dysferlin protein is used as a diagnostic indicator of dysferlin deficiency.

A number of embodiments of the invention have been described. Nevertheless, it will be understood that various modifications may be made without departing from the spirit and scope of the invention. Accordingly, other embodiments are within the scope of the following claims.

TABLE 1

Evaluation of Dysferlin Deficiency by Immunodiagnosis in Peripheral Blood Mononuclear Cells (PBMC) and Skeletal Muscle.

| Patient | Clinical diagnosis | Mutation | Dysferlin expression in PBMC | Dysferlin expression in skeletal muscle | Immunocytochemical analysis of PBMC |
|---|---|---|---|---|---|
| RB 2329 | MM | E1883X, 6319 + 1G | (−) | (−) | (−) |
| RB 1859 | MM | deletion AG, at 6071 | (−) | (−) | n.d. |
| RB 2079 | DACM | deletion G at 5966 | (−) | (−) | (−) |
| II 1101 | MM | n.d. | (−) | (−) | (−) |
| II 1102 | MM | n.d. | (−) | (−) | (−) |
| II 1103 | MM | n.d. | (−) | (−) | (−) |
| II 1104 | MM | n.d. | (−) | (−) | (−) |
| II 1303 | LGMD 2B | n.d. | (−) | (−) | (−) |
| II 1304 | LGMD 2B | n.d. | (−) | (−) | (−) |
| II 1305 | LGMD 2B | n.d. | (−) | (−) | (−) |
| II 1306 | LGMD 2B | n.d. | (−) | (−) | (−) |
| RB 3533 | MM | n.d. | (−) | (−) | n.d. |

MM, Miyoshi myopathy;
LGMD 2B, limb girdle muscular dystrophy;
DACM, distal anterior compartment myopathy (ref 7);
X = stop codon;
n.d., not determined;
PBMC, peripheral blood mononuclear cells;
(−) = absence of dysferlin staining. For positive controls, 6 of 6 PBMC samples obtained from healthy individuals showed positive dysferlin reactivity by Western blot analysis.

What is claimed is:

1. A method of determining whether dysferlin is expressed in a mammal, the method comprising
    (a) providing a blood sample from the mammal, and
    (b) assaying the blood sample for the presence of dysferlin expression.

2. The method of claim 1, wherein step (b) comprises detecting dysferlin nucleic acid expression.

3. The method of claim 1, wherein step (b) comprises detecting dysferlin protein expression.

4. The method of claim 3, wherein step (b) comprises an immunologic assay.

5. The method of claim 1, wherein the mammal is suspected of having a dysferlinopathy.

6. The method of claim 5, wherein the dysferlinopathy is limb girdle muscular dystrophy 2B (LGMD) or Miyoshi myopathy (MM).

7. The method of claim 1, further comprising the step of determining the level of dysferlin protein or dysferlin mRNA in the blood sample.

8. The method of claim 1, further comprising the step of comparing the level of dysferlin protein or dysferlin mRNA in the blood sample to a reference, wherein the reference is a value obtained from a blood sample from an individual who does not have a dvsferlinopathy.

9. The method of claim 8, wherein a lower level of dysferlin expression in the blood sample compared to the reference indicates the presence of a dysferlinopathy in the mammal.

10. The method of any of claims 1–9, wherein the mammal is a human.

11. A method of determining whether a mammal has a dysferlinopathy, is predisposed to having a dysferlinopathy, or is a genetic carrier for a dysferlinopathy, the method comprising (a) providing a blood sample from the mammal; and (b) determining the level of dysferlin expression in the blood sample, wherein a level lower than a reference, wherein the reference is a value obtained from a blood samDle from an individual who does not have a dysferlinopathy, is an indication that the mammal has a dysferlinopathy, is predisposed to having a dysferlinopathy or is a genetic carrier for a dysferlinopathy.

12. The method of claim 11, wherein the step of determining the level of dysferlin expression comprises exposing the blood sample to a dysferlin nucleic acid probe that hybridizes to a dysferlin mRNA.

13. The method of claim 11, wherein the step of determining the level of dysferlin expression comprises detecting the presence of dysferlin polypeptide.

14. The method of claim 13, wherein the step of determining the level of dysferlin expression comprises exposing the blood sample to an anti-dysferlin antibody.

15. The method of claim 11, wherein the mammal is a human.

16. The method of claim 11, wherein the dysferlinopathy is limb girdle muscular dystrophy or Miyoshi myopathy.

* * * * *